United States Patent [19]
Bergstrom et al.

[11] Patent Number: 5,096,923
[45] Date of Patent: Mar. 17, 1992

[54] SQUALENE SYNTHETASE INHIBITORS

[75] Inventors: James D. Bergstrom, Neshanic; Otto D. Hensens, Red Bank; Leeyuan Huang, Watchung; Jerrold M. Liesch, Princeton Junction; Janet C. Onishi, Mountainside; Frank L. Vanmiddlesworth, Fanwood, all of N.J.

[73] Assignee: Merck & Co., Inc., Rahway, N.J.

[21] Appl. No.: 496,742

[22] Filed: Mar. 21, 1990

[51] Int. Cl.$^5$ .................. A61K 31/335; C07D 319/08
[52] U.S. Cl. ..................................... 514/452; 549/363
[58] Field of Search .......................... 549/363; 514/452

[56]  References Cited
U.S. PATENT DOCUMENTS
4,871,721  10/1989  Biller ................................... 514/102

FOREIGN PATENT DOCUMENTS
0405864A2  1/1991  European Pat. Off. .

OTHER PUBLICATIONS
S. A. Biller et al., *J. Med. Chem.*, 31, 1869 (1988).
C. D. Poulter et al., *J. Am. Chem. Soc.*, 111, 3734 (1989).
E. J. Corey et al., *J. Am. Chem. Soc.*, 98, 1291 (1976).

*Primary Examiner*—Nicky Chan
*Attorney, Agent, or Firm*—Joseph F. DiPrima; Melvin Winokur

[57]  ABSTRACT

This invention relates to compounds of structural formula (I):

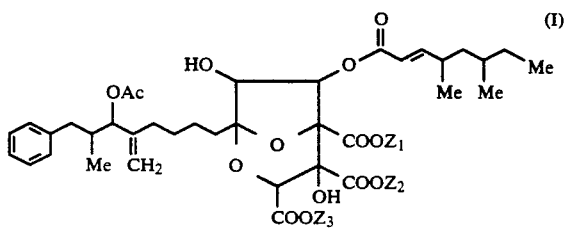

which are squalene synthetase inhibitors and thus useful as cholesterol lowering agents.

14 Claims, 2 Drawing Sheets

SQUALENE SYNTHETASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

The present invention provides nonphosphorus containing inhibitors of squalene synthetase.

DETAILED DESCRIPTION OF THE INVENTION

Figure 1:
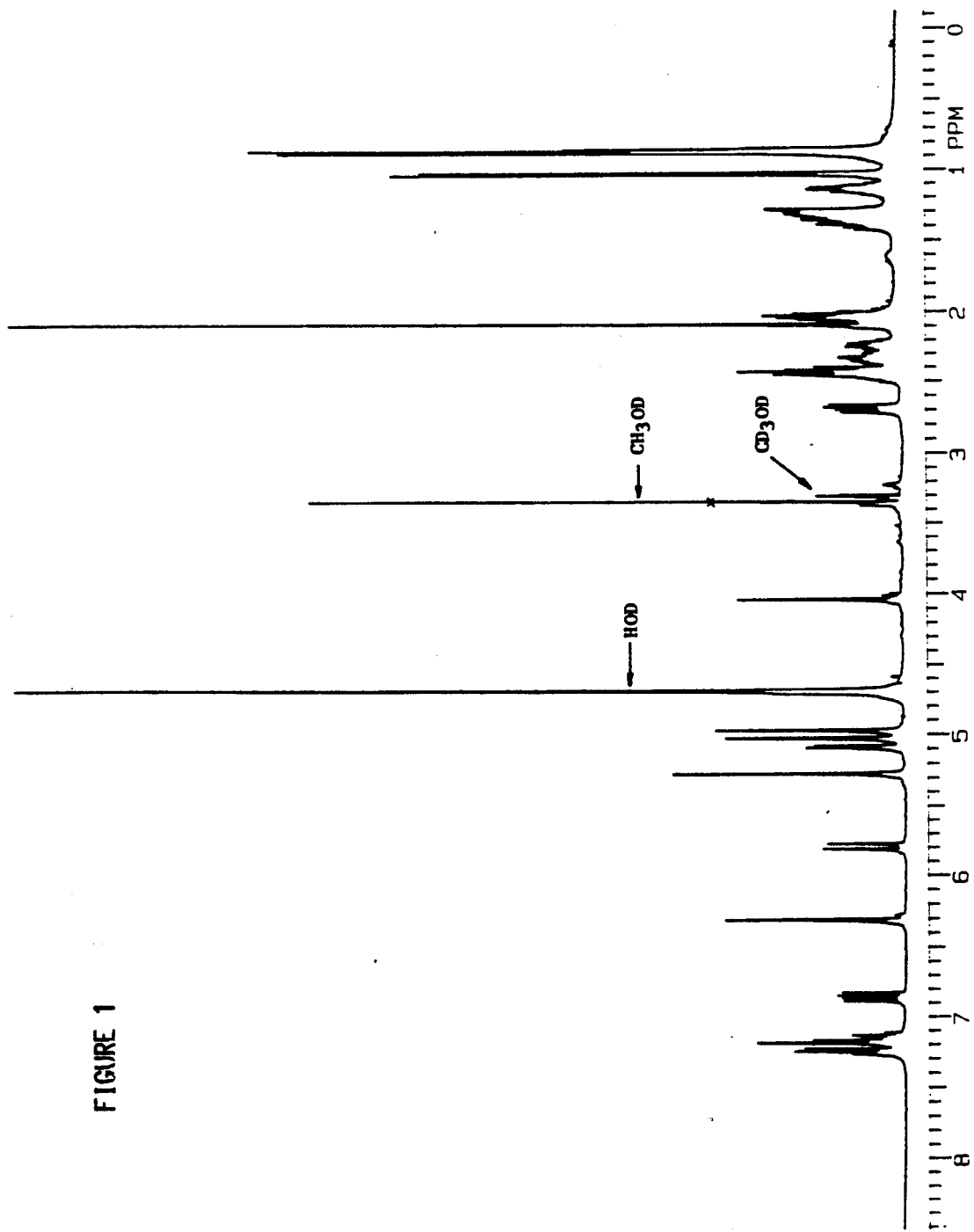

The present invention is directed to novel compounds of structural formula (I) which are squalene synthetase inhibitors:

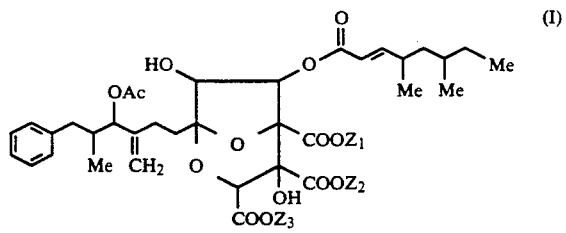

wherein
$Z_1$, $Z_2$ and $Z_3$ are each independently selected from;
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, I, F) or hydroxy; or
a pharmaceutically acceptable salt of a compound of of formula (I) in which at least one of $Z_1$, $Z_2$ and $Z_3$ is hydrogen.

In one embodiment of the present invention are those compounds of formula (I) wherein the relative stereochemical configuration of the 2,8-dioxabicyclo[3.2.1]octane ring is as shown below:

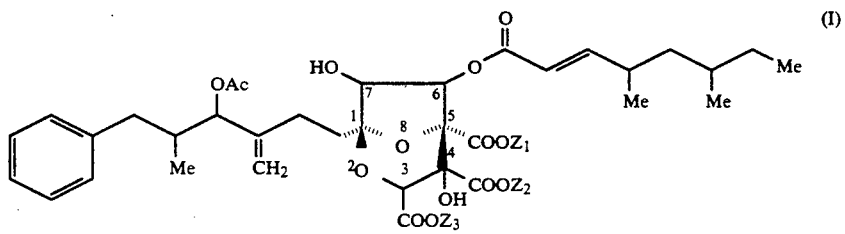

Throughout this specification and claims where stereochemistry is described for the dioxabicyclo[3.2.1]octane ring the configuration implied is relative. The actual configuration may be as shown or that of its enantiomer.

Further illustrating this embodiment are those compounds of structural formula (I) wherein the relative configuration at positions 3, 6 and 7 is as shown below:

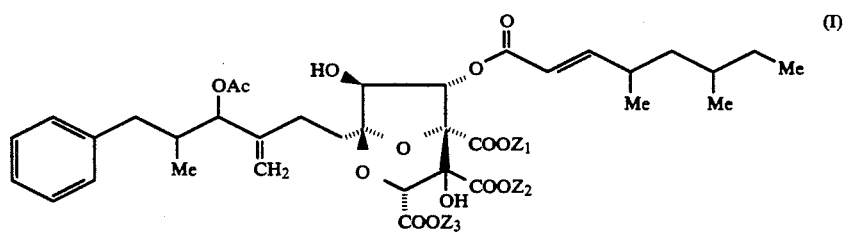

In one class of this embodiment are those compounds of structure (I) wherein the relative configuration at the 4-position is as shown below:

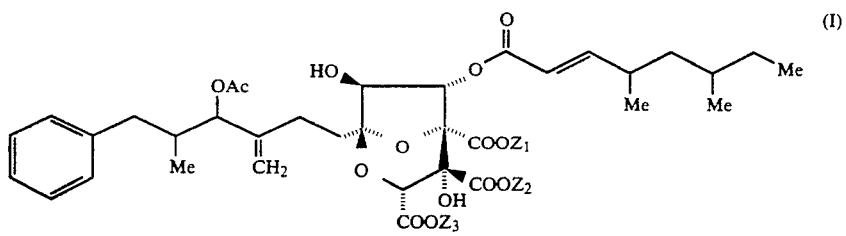

Exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as compound A.

Further illustrating this class are those compounds in which one or more of $Z_1$, $Z_2$ or $Z_3$ is $C_{1-5}$alkyl or $C_{1-5}$alkyl substituted with phenyl or phenyl substituted with methyl, methoxy, halogen (Cl, Be, I, F) or hydroxy. In a specific illustration, $Z_1$, $Z_2$ and $Z_3$ are each methyl. This compound is hereafter referred to as compound B.

The compounds of formula (I) are prepared in an aerobic fermentation procedure employing a novel culture, MF5453, observed as a sterile mycelium. Mutants of MF5453 are also capable of producing compounds of this invention.

The culture MF5453 is that of a fungus isolated from a water sample obtained from the Jalon river, Zaragoza, Spain. This culture has been deposited with the American Type Culture Collection at 12301 Parklawn Drive, Rockville, MD 20852 as ATCC 20986.

The microorganism MF5453 exhibits the following morphological characteristics:

Colonies 22-24 mm in diameter in two weeks on potato-dextrose agar (Difco) at 25° C. in continuous fluorescent light, 40-45 mm diameter in two weeks on deer dung-extract agar (*Mycology Guidebook*, media M-11, p. 660) at 25° C. Colonies on potato-dextrose agar consisting of moderately thick, 1-2 mm deep, mycelium, cottony at the center, becoming felty to velutinous towards the margin, forming obscure concentric ridges, occasionally forming sectors of differing mycelial texture and color, margin entire, without a fringe of submerged leading hyphae. Colony color at first white or some white aerial hyphae, soon becoming cream, Cream Color, Cartridge Buff, (capitalized color names from Ridgway, R. *Color Standards and Nomenclature*, Washington, D.C. 1912), finally light gray to gray, Light Olive-Gray, Gray, Pallid Neutral Gray, Neutral Gray, Gull Gray, Deep Gull Gray. Colony reverse grayish brown to yellow brown or cream, Cinnamon-Drab, Cinnamon, Ochraceous-Buff, Antimony Yellow, Warm Buff, Cartridge Buff. Odors and exudates absent.

Hyphae ascomycetous in morphology, undifferentiated, septate, branched 1.5-3.5 μm in diameter, hyaline in water and KOH. No reproductive structures formed on any of cultural conditions surveyed, including incubation in both continuous light and 12/12 hour dark cycles on either cornmeal agar, hay extract agar, oatmeal agar, dung extract agar, and malt extract agar.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 90 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salt and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar condition but employing shorter time.

After inoculation, the fermentation production medium is incubated for 3 to 30 days, preferably 4 to 14 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.55 to 8.5, most preferably 5.0 to 7.5. After the appropriate period for production of the desired compound, fermentation flasks are harvested and the active compound isolated.

The pH of the aqueous mycelial fermentation is adjusted to between 1 and 9 (preferably between 3 and 5) preferably mixed with a water miscible solvent such as 50% methanol and the mycelia filtered. The active compound may then be isolated from the aqueous filtrate by several methods including:

1. Liquid-liquid extraction of the aqueous filtrate into a water immiscible solvent such as methyl elthyl ketone, ethyl acetate, diethyl ether, or dichloromethane preferably after having adjusted the pH to between 3 and 5.

2. Solid-liquid extraction of the aqueous filtrate onto an organic matrix such as SP207 or HP-20 and elution with an organic solvent (aqueous or non aqueous) such as 90/10 methanol/water or 90/10 acetone/water.

3. Adsorption of the active compound from the aqueous filtrate onto an ionic exchange resin such as Dowex 1($Cl^-$) or Dowex 50 ($Ca^{2+}$) and elution with a high ionic strength organic/aqueous solvent such as 90/10 methanol/aqueous 30% $NH_4Cl$. This material could then be desalted by employing either method 1 or 2 above.

Each of these three methods may also be used in the further purification of the active compound.

The fraction containing active compound from the above methods could then be dried in vacuo leaving the crude active compound. The crude active compound is then generally subjected to several separation steps such as adsorption and partition chromatography, and precipitation. For each separation step, fractions are collected and combined based on results from an assay and/or HPLC analysis.

The chromatographic separations may be carried out by employing conventional column chromatography with ionic or nonionic adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. The active compound can be precipitated out of a non-polar solvent as the quinine salt. The preferred solvent for precipitation is diethyl ether.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. This invention includes salts of one, two or three of the carboxyl groups of formula (I).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic squalene synthetase inhibitory activity of representative compounds of this invention was measured by the standard in vitro protocol described below:

PREPARATION OF MICROSOMES

Male, Charles River CD rats (120 to 150 g) were fed a diet containing 0.1% lovastatin for 4 days. The livers from these rats were homogenized in 5 volumes (ml/g) of ice cold 50 mM HEPES (4-(2 -hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

PARTIAL PURIFICATION OF PRENYL TRANSFERASE

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5. with 6N HOAc and centrifuged at 100,000×g for 1 hour. This supernatant was adjusted to pH 7.0 with 3N KOH and a 35–60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm colum of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM $\beta$-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

ENZYMATIC SYNTHESIS OF [4-$^{14}$C]FARNESYL-PYROPHOSPHATE

The solvent (ethanol: 0.15N NH$_4$OH, 1:1) was removed from 55 $\mu$Ci of [4-$^{14}$C]isopentenyl pyrophosphate (47.9 $\mu$Ci/$\mu$mole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 $\mu$l of a 20 mM solution, and 50 $\mu$l of the ammonium sulfate suspension of prenyl transferase were added to initiate the reaction. This incubation contained 5 $\mu$moles of geranyl pyrophosphate, 1.15 $\mu$moles of isopentenyl pyrophosphate, 6 $\mu$moles of MgCl$_2$ and 0.18 units of prenyl transferase in a volume of 900 $\mu$l. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5. The yield was 50.7 $\mu$Ci (92%) of [4-$^{14}$C]farnesyl pyrophosphate. The [4-$^{14}$C]farnesyl pyrophosphate was stored in aliquots at $-70°$ C.

SQUALENE SYNTHETASE ASSAY

Reaction were performed in 16×125 mm screw cap test tubes. A batch assay mix was prepared from the following solution:

|  | $\mu$l per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate | 3.0 | 150 |

-continued

|  | $\mu$l per assay | volume for 50 assays |
|---|---|---|
| 47.9 $\mu$Ci/$\mu$mole, and 0.025 $\mu$Ci/3.0 $\mu$l |  |  |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 $\mu$l of the assay mix was taken with 3 $\mu$l of an inhibitor solution (DMSO or MeOH in the controls), warmed to 30° C. in a water bath and then the reaction was initiated by the addition of 10 $\mu$l of the 1:120 dilution of microsomal protein (0.6 $\mu$g protein total in the assay). The reactions were stopped after 20 minutes by the addition of 100 $\mu$l of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that give 50% inhibition as determined from these plots.

Representative of the intrinsic squalene synthetase inhibitory activities of the compounds of this invention are the IC$_{50}$ data tabulated below:

| Compound | Squalene Synthetase ID$_{50}$ |
|---|---|
| Compound A | 5 nM |
| Compound B | 5 $\mu$M |

The present compounds also demonstrate broad spectrum antifungal activity as determined by broth or agar dilution methods. The compounds are particularly active towards filamentous fungi and yeasts including *Candida albicans* and *Crypt neoformans*. The sensitivity of filamentous fungi and yeast was determined using inhibitor dilution assays in microtiter format. The compounds were dissolved in DMSO at 2 mg/ml and serially diluted in 0.1M phosphate buffer, pH 7.0 in the microtiter dish from 100 to 0.006 $\mu$g/ml. A standardized spore suspension for testing the filamentous fungi was prepared by inoculating Antibiotic Medium #3 containing 1.5% agar with spores such that 1.5×10$^3$ colony forming units were added per well. The microtiter wells were filled with 50 $\mu$l of buffer containing compound and 50 $\mu$l of inoculated medium. The sensitivity of yeasts was determined by inoculating yeast nitrogen base containing 1% dextrose (YNB/G) with aliquots of an overnight yeast culture grown in yeast morphology (YM) media at 35° C. and diluting in YNB/G to yield a final concentration of 1.5–7.5×10³ colony forming units/well. One hundred fifty μl of inoculated media was added per well. To test the sensitivity of yeast, compound was solubilized in 10 percent aqueous DMSO at 2.56 mg/ml. The compound was diluted serially in YNB/G from 128 to 0.06 μg/ml. The wells were filled with 150 μl of drug containing media. The minimum inhibitory concentration (MIC) is defined as the lowest concentration to prevent visible growth after an incubation for 42 hours, 28° C. for the filamentous fungi and 24 hours, 28° C. for the yeasts. Representative of the antifungal activity are the minimum inhibitory concentration data shown below.

| Minimum Inhibitory Concentration (mcg/ml) | |
| --- | --- |
| Organism | Compound B |
| Filamentous Fungi | |
| A. fumigatus MF4839 | 6.2 |
| A. flavus MF383 | 6.2 |
| A. niger MF442 | 25 |
| Fus. oxysporum MF4014 | >100 |
| Pen. italicum MF2819 | 6.2 |
| Coch. miyabeanus MF4626 | 1.6 |
| Yeast | |
| C. albicans MY1055 | 8 |
| C. tropicalis MY1012 | 4 |
| C. parapsilosis MY1010 | 8 |
| Crypt. neoformans MY1051 | 1 |

Thus the present invention is also directed to a method of treating fungus infections which comprises the administration to an organism in need of such treatment of a nontoxic therapeutically effective amount of a compound represented by the structural formula (I) and pharmaceutically acceptable salts thereof. Based on the above MIC data it is determined that generally form 2 to about 5 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals, such as man, or birds, or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers kaolin, ethyl cellulose, surface active dispersing agents, generally with a lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following examples illustrate the preparation of the compounds of formula (I) and their incorporation into pharmaceutical compositions and as such are not to be considered as limiting the invention set forth in the claims appended hereto. The preferred route to Compound A is Example 2.

The composition of media employed in the following Examples are listed below:

| KF SEED MEDIUM | per liter | Trace Elements Mix | g/L |
| --- | --- | --- | --- |
| Corn Steep Liquor | 5 g | FeSO$_4$.7H$_2$O | 1.0 |
| Tomato Paste | 40 g | MnSO$_4$.4H$_2$O | 1.0 |
| Oat Flour | 10 g | CuCl$_2$.2H$_2$O | 0.025 |
| Glucose | 10 g | CaCl$_2$.2H$_2$O | 0.1 |
| Trace Element Mix | 10 ml | H$_3$BO$_3$ | 0.056 |
| pH adjusted to 6.8 (presterile) | | (NH$_4$)$_6$Mo$_7$O$_{24}$.4H$_2$O | 0.019 |
| 50 mls/nonbaffled Erlenmeyer flask autoclave 20 minutes (121° C., 15 psi) | 250 mls | ZnSO$_4$.7H$_2$O dissolved in 1 L 0.6 N HCl | 0.2 |

| MBM Production Medium | g/L |
| --- | --- |
| Malt extract (Difco) | 5.0 |
| Glucose | 15.0 |
| Peptone | 1.0 |
| KH$_2$PO$_4$ | 1.0 |
| MgSO$_4$ | 0.5 |
| distilled H$_2$O (no pH adjustment) 45 mls/nonbaffled 250 mls Erlenmeyer flask autoclave 15 min- | 1000.0 mls |

-continued utes (121° C., 15 psi)

EXAMPLE 1

Preparation of Compound A

A. Culturing MF5453

Culture MF5453 was inoculated into KF seed medium using one glass scoop of the original soil tube. The KF seed flask was incubated for 73 hours at 25° C., 220 rpm, 85% humidity. At the end of this incubation, 2.0 mls aliquots were aseptically transferred to each of 75 MBM production medium flasks. These production flasks were then incubated at 25° C., 220 rpm, 85% humidity, with a fermentation cycle of 14 days. Flasks were harvested as follows: mycelial growth was homogenized for 20 seconds at high speed using a Biohomogenizer/mixer (Biospec Products Inc. Bartlesville, Ok); and then 45 mls methanol was added to each flask (final methanol concentration was approximately 50%). Flasks were then returned to the shaker and agitated at 220 rpm for 30 minutes. Subsequently, the contents of the flasks were pooled.

B. Isolation of Compound A

A 6 liter 50% methanol homogenized fungal extract exhibiting a pH of 4.5 was employed in the following isolation procedure. The mycelia was filtered through celite and the recovered mycelia was extracted again by stirring overnight with 3 L of 50% methanol and again filtered.

The combined extract (9 L) of 50% methanol was diluted to 25% methanol with water (total volume 18 L) and applied to a Mitsubishi HP-20 column (750 ml) at a flow rate of 80 ml/minute. The column was washed with water (1 L) and eluted with a stepwise gradient of methanol consisting of 50/50 methanol/$H_2O$ (1 L), 60/40, methanol/$H_2O$ (1 L), 80/20 methanol/$H_2O$ (2 L,) 90/10 methanol/$H_2O$ (1 L), 100% methanol (2 L), and 100% acetone (1 L). The fractions from 50/50 to 90/10 methanol/$H_2O$ were combined and diluted with water to 35/65 methanol/$H_2O$ (total volume 10 L).

The 10 L of 35/65 methanol/$H_2O$ was acidified with 1.0N HCl (20 ml) to pH 3.0 and extracted into EtOAc (4 L). The EtOAc layer was separated and the solvent removed in vacuo to yield 260 mg of an orange oil.

A portion (10%) of the orange oil was dissolved in 1 ml methanol and diluted with 0.8 ml 10 mM potassium phosphate (pH 6.5) with some precipitation. The suspension was applied to a preparative HPLC column (Whatman Magnum 20 $C_{18}$, 22 mm ID X 25 cm, 8 ml/minute. The initial mobile phase was 60/40 methanol/10 mM $K_3PO_4$, pH 6.5, and after 20 minutes the mobile phase was changed to 80/20 methanol/10 mM potassium phosphate, pH 6.5. Fractions of 8 ml each were collected, and the fractions from 31 to 33 minutes (2) were combined, diluted with water to 35% methanol, acidified with 10% HCl to pH 3, and extracted into EtOAc. The solvent was removed in vacuo and a clear slightly yellow oil identified as the titled compound was obtained.

EXAMPLE 2

Preparation of Compound A

A. Culturing MF5453

A 250 mL Erlenmeyer flask containing 54 mL of the seed medium (KF) was inoculated with MF5453 and incubated at 25° C. and 85% humidity at 220 rpm for 72 hours. Ten mL of the culture was transferred to each of three 2-liter Erlenmeyer flasks containing 500 mL of the KF seed medium. These flasks were cultivated for 44 hours at 25° C., 85% humidity at 220 rpm. Seven hundred fifty mL of the resulting culture were used to inoculate each of 2 22-Liter fermentors containing 15 Liters of MBM production medium. Sterilization conditions were as follows: 122° C., 15 psi for 25 minutes. The pH of the medium after sterilization was 5.0. The fermentation conditions were as follows: 25° C., at an agitation rate of 300 rpm, and airflow rate of 4.5 liters per minute, and a back pressure of 5 psi. After 357 hours of cultivation under these conditions the batches were harvested.

B. Isolation of Compound A

Three independent fermentations (3 L), (10 L), and (10 L) were employed in the following isolation procedure. The 3 L fermentation was cultured following Example 1A and each 10 L fermentation was cultured following the procedure of Example 2A. Each fermentation was filtered through celite and the mycelia extracted individually overnight (2×) with 1 L, 3 L, and 3 L 50% methanol respectively.

The filtrates and extracts were all combined and diluted with water to 25% methanol (total volume 45 L). This was applied to a Mitsubishi HP-20 column (1.5 L) at a flow rate of 100 ml/minute. The column was then washed with water (4 L), and 40% methanol (6 L). The column was then eluted with 100% methanol (6 L).

The 100% methanol HP-20 eluate was diluted with 10 mM $H_3PO_4$ (6 L, total volume 12 L) and extracted into $CH_2Cl_2$ (4 L). The solvent was removed in vacuo to yield 21 g of a yellow oil.

The above concentrate was dissolved in methanol (500 ml) and diluted with 20 mM $K_3PO_4$, pH 7.0 (500 ml). This solution was applied to a Dowex 1×2 (Cl$^-$) column (350 ml) at a rate of 25 ml/minute. The column was washed with 50/50 methanol/water (2 L), 50/50 methanol/3% NaCl solution (1 L), and the product was eluted with 90/10 methanol/30% aqueous $NH_4Cl$ solution (2 L). The methanol/$NH_4Cl$ eluate was diluted with 20 mM $H_3PO_4$ (2 L) and extracted with $CH_2Cl_2$ (2 L). The solvent was removed in vacuo to yield a thick orange oil.

A portion of the orange oil (24 mg) was dissolved in 1 ml methanol and 0.4 ml of 10 mM $H_3PO_4$ was added with some clouding. This suspension was applied to a preparative HPLC column (Whatman Magnum 20 $C_{18}$, 22 mm ID×25 cm, 8 ml/minute, mobile phase 80/20 methanol/10 mM $H_3PO_4$ pH 2.5). The fractions eluting between 16 and 20 minutes were combined. diluted with 50 mM $H_3PO_4$ (50 ml), and extracted with $CH_2Cl_2$ (2×75 ml). The $CH_2Cl_2$ was removed in vacuo to yield a slightly yellowed oil. This material exhibited identical $^1H$-NMR and UV spectra with that of Compound A isolated in Example 1.

EXAMPLE 3

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

EXAMPLE 4

Preparation of an Ammonium Salt

A 0.1 mmol sample of the free acid of Compound (I) is dissolved in 10 ml of ethyl acetate. The resulting solution is saturated with gaseous ammonia, upon which the ammonium salt precipitates from solution.

EXAMPLE 5

Preparation of Potassium Salt

A solution of 0.1 mmol of the free acid of Compound (I) in 10 ml of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts of Compound (I) can be formed.

EXAMPLE 6

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 7

Preparation of an ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N''-dibenzylethylenediamine salt.

EXAMPLE 8

Preparation of a Tris(hydroxymethyl)aminomethane salt

To a solution of 0.1 mmol of the free acid of a Compound of formula (I) in 10 ml of methanol is added from 0.1 to 0.3 mmol of tris(hydroxymethyl)aminomethane dissolved in 10 ml of methanol. Evaporation of the solvent gives a corresponding salt form of Compound (I) exact composition of which is determined by the molar ratio of amine added.

The method can also be applied to other amines such as, but not limited to: diethanolamine and diethylamine.

EXAMPLE 9

The preparation of a L-arginine salt

To a solution of 0.1 mmol of the free acid of a compound of formula (I) in 10 ml of 6:4 methanol/water is treated with an aqueous solution of 0.1–0.3 mmol of L-arginine. Evaporation of the solvent affords the title salt, the exact composition of which is determined by the molar ratio of amino acid to the feee acid of Compound (I).

Similarly prepared are the salts of L-ornithine, L-lysine, and N-methylglucamine.

EXAMPLE 10

Preparation of Compound B (Method 1)

A solution of 90 mg of Compound A in 5 ml of ethyl acetate was treated with a slight excess of ethereal diazomethane. After 5 minutes excess diazomethane was removed and the solvent was evaporated to give Compound B.

EXAMPLE 11

Preparation of Compound B

A solution of 2 mg of Compound A in 0.5 ml of acetonitrile was treated at room temperature with 10 equivalents of DBU and 10 equivalents of MeI. After 2 hours the reaction was diluted with 10 ml of dichloromethane and washed successively with 10 ml of 0.1M phosphoric acid, 10 ml of water, 10 ml of saturated sodium bicarbonate and 10 ml of water. After drying over sodium sulfate, the organic layer was concentrated and the residue was chromatographed on silica gel using mixtures of hexane and ethyl acetate to give Compound B.

The method of Example 11 is also suitable for the preparation of other ester derivatives such as 1) ethyl and other lower alkyl esters and 2) benzyl and substituted benzyl esters.

Mass Spectral Data

Mass spectra were recorded on Finnigan-MAT model MAT212 (electron impact, EI, 90 eV), MAT 90 (Fast Atom Bombardment, FAB), and TSQ70B (FAB, EI mass spectrometers. Exact mass measurements were performed at high resolution (HR-EI) using perfluorokerosene (PFK) or perfluoropolypropylene oxide (Ultramark U1600F) as internal standard. Trimethylsilyl derivatives were prepared with a 1:1 mixture of BSTFA-pyridine at room temperature.

$^{13}$C NMR Data

The $^{13}$C NMR spectrum of Compound A was recorded in CD$_3$OD at 100 MHz on a Varian XL400 spectrometer. Chemical shifts are given in ppm relative to tetramethylsilane (TMS) at zero ppm using the solvent peak at 49.0 ppm as internal standard. The $^{13}$C NMR spectrum of Compound B was recorded at 75 MHz (ambient temperature) on a Varian XL300 spectrometer in C$_6$D$_6$ using the solvent peak at 128.0 ppm as internal standard.

$^1$H NMR Spectra

The $^1$H NMR spectra were recorded at 400 MHz in CD$_3$OD and C$_6$D$_6$ on a Varian XL400 spectrometer. Chemical shifts are shown in ppm relative to TMS at zero ppm using the solvent peaks at 3.30 ppm (CD$_3$OD) and 7.15 ppm (C$_6$D$_6$) as internal standards.

Physical Properties of the compounds of Structure I

Compound A—the compound of structure (I) wherein $Z_1$ $Z_2$ and $Z_3$ are each hydrogen.

Mass Spectral Data

This compound has the molecular weight 690 by FAB-MS (observed [M+H]$^+$ at m/z 691, and with addition of lithium acetate [M.Li$_3$+Li]$^+$ (i.e., the lithium adduct of the trilithium salt) at m/z 715). The molecular formula C$_{35}$H$_{46}$O$_{14}$ was determined by HR-EI measurement of the penta-trimethylsilyl derivative (calc for C$_{35}$H$_{46}$O$_{14}$+(SiC$_3$H$_8$)$_5$ 1050.4864, found 1050.4829). Other critical fragment ions were observed in the silyl spectrum as follows: [M-AcOH]+, calc for $C_{33}H_{44}O_{13}+(SiC_3H_8)_5$ 990.4597, found 990.4625; $C_{23}H_{25}O_{10}+(SiC_3H_8)_4$, calc 749.3015, found 749.3022; [M-(CO$_2$H+SiC$_3$H$_8$)]+, calc for $C_{34}H_{45}O_{12}+-(SiC_3H_8)_4$ 933.4458, found 933.4450; $C_{16}H_{23}O_8+-(SiC_3H_8)_4$, calc 631.2974, found 631.2944.

$^1$H NMR Spectrum (CD$_3$OD, 40° C.): See FIG. 1.

$^{13}$C NMR Chemical Shifts (CD$_3$OD, 40° C.): 11.5, 14.3, 19.4, 20.6, 21.0, 26.7, 30.8, 33.3, 35.2, 35.6, 37.9, 41.0, 44.5, 75.8, 76.8, 80.4, 81.3, 82.7, 91.3, 106.9, 111.7, 120.0, 127.0, 129.4 (2×), 130.3(2×), 141.7, 147.9, 157.6, 166.8, 168.7, 170.3, 172.2, 172.7 ppm.

UV(MeOH) λmax 209 nm (ε=36,000).

IR(as free acid; film on ZnSe): 3400-2500 br, 2960, 2930, 2875, 1745-1700, 1650, 1450, 1375, 1280-1225, 1185, 1135, 1020, 985, 750, and 700 cm$^{-1}$.

Compound B—the trimethyl ester of Compound A, i.e., the compound of structure (I) wherein $Z_1$, $Z_2$ and $Z_3$ are each methyl.

Mass Spectral Data

This compound has the molecular weight 732 by EI-MS and forms a di-(trimethylsilyl) derivative. The molecular formula $C_{38}H_{52}O_{14}$ was determined directly by HR-EI measurement (calc 732.3357, found 732.3329).

Figure 2:
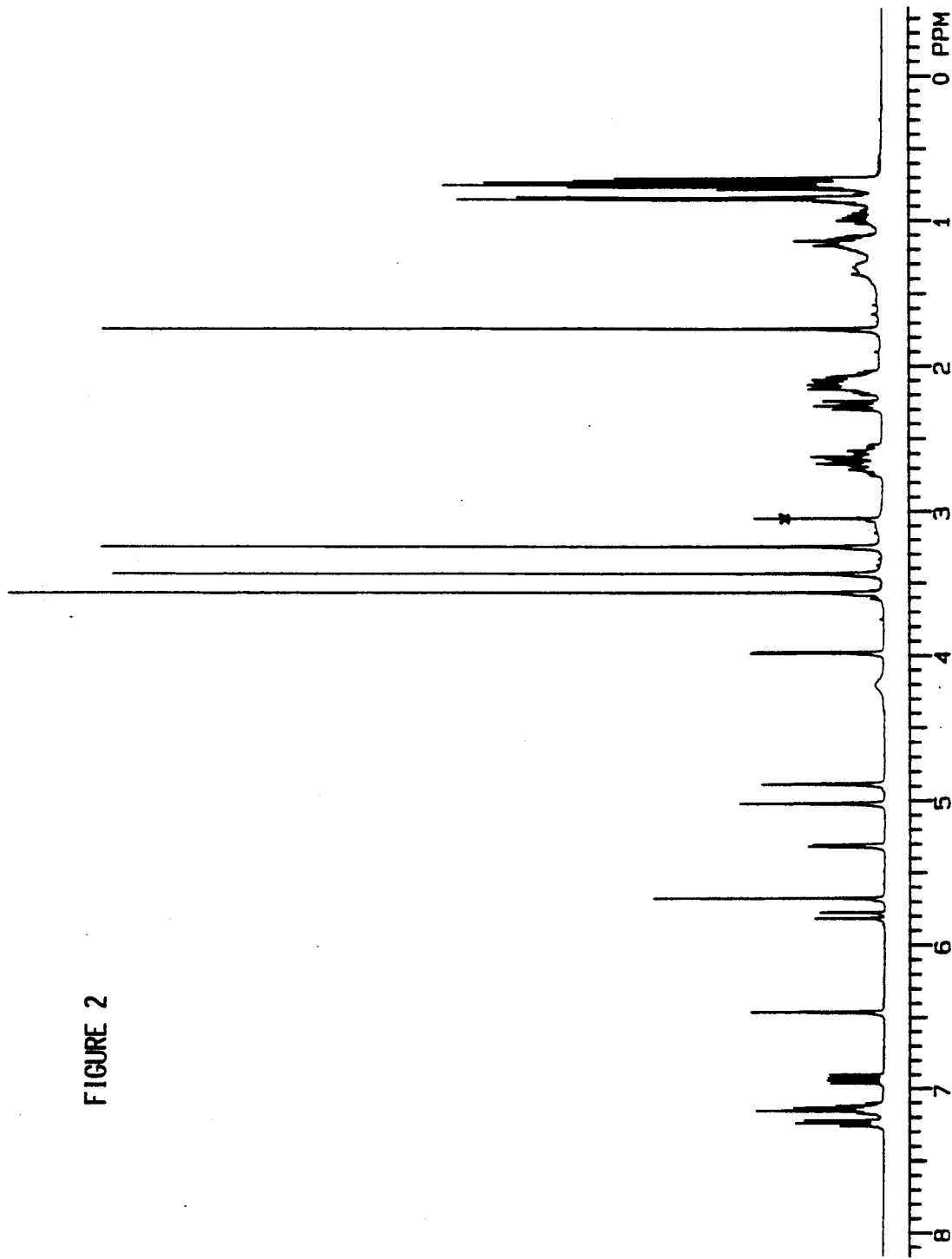

$^1$H NMR Spectrum(C$_6$D$_6$, 22° C.): See FIG. 2.
$^{13}$C NMR Chemical Shifts (C$_6$D$_6$, 75 MHz): 11.3, 14.0, 18.9, 20.2, 20.6, 26.3, 30.0, 32.1, 34.6, 34.7, 37.1, 40.2, 43.3, 51.9, 52.1, 53.3, 75.3, 76.2, 78.8, 82.0, 82.8, 89.8, 106.2, 111.8, 118.8, 126.2, 128.6(2×), 129.6(2×), 140.9, 146.6, 157.2, 166.0, 166.5, 167.2, 169.5, 170.3 ppm.

What is claimed is:

1. A compound of structural formula (I)

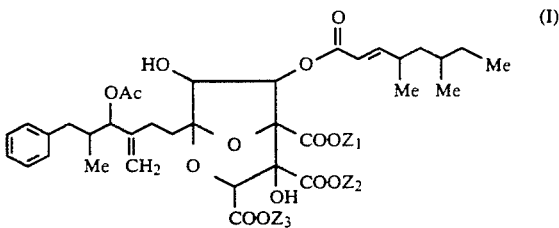

wherein
$Z_1$ $Z_2$ and $Z_3$ are each independently selected from
a) H;
b) C$_{1-5}$ alkyl;
c) C$_{1-5}$ alkyl substituted with a member of the group consisting of
i) phenyl,
ii) phenyl substituted with methyl, methoxy, halogen (Cl, Br, I, F) or hydroxy; or
a pharmaceutically acceptable salt of a compound of formula (I) in which at least one of $Z_1$, $Z_2$ and $Z_3$ is hydrogen.

2. A compound of claim 1 wherein the relative configuration within structural formula (I) is:

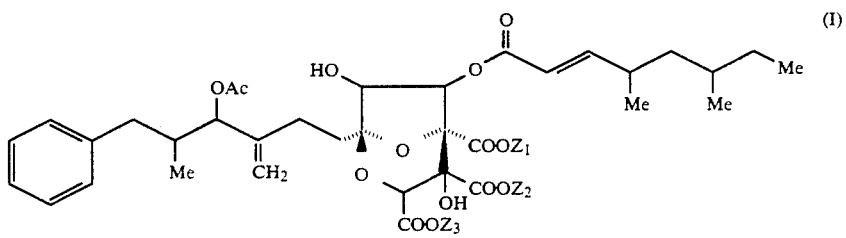

3. A compound of claim 2 wherein the relative configuration within structural formula (I) is:

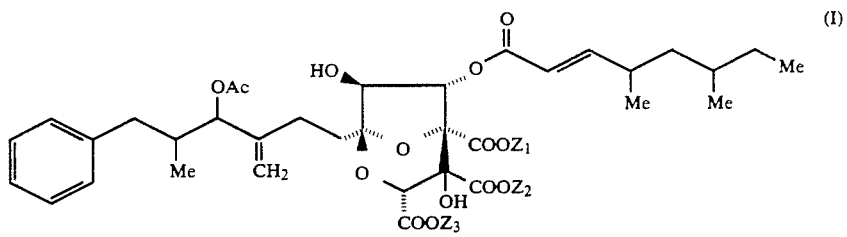

4. A compound of claim 3 wherein the relative configuration of structural formula (I) is:

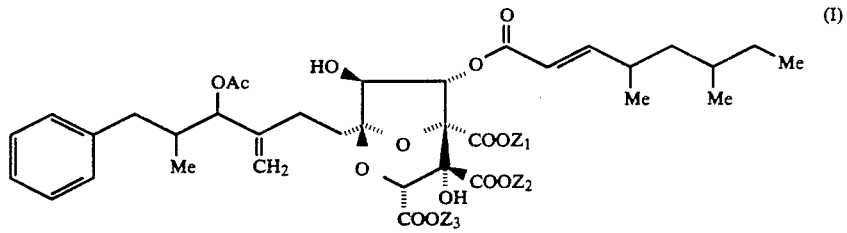

5. A compound of claim 4 in which $Z_1$, $Z_2$ and $Z_3$ are each hydrogen or a pharmaceutically acceptable salt thereof.

6. A compound of claim 4 in which $Z_1$, $Z_2$ and $Z_3$ are each methyl.

7. A compound of claim 1 which is:

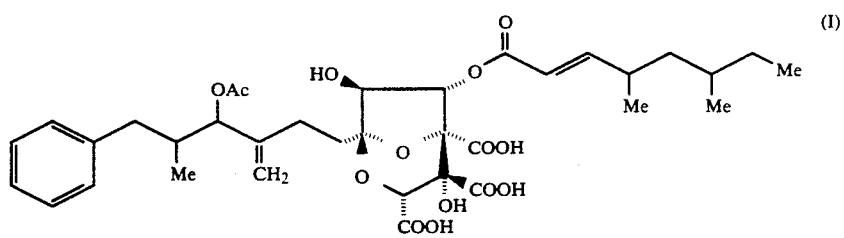

8. A pharmaceutical composition comprising a nontoxic therapeutically effective amount of a compound of claim 1 and a pharmaceutically acceptable carrier.

9. A composition of claim 8 wherein the therapeutically effective compound is selected from the group consisting of:

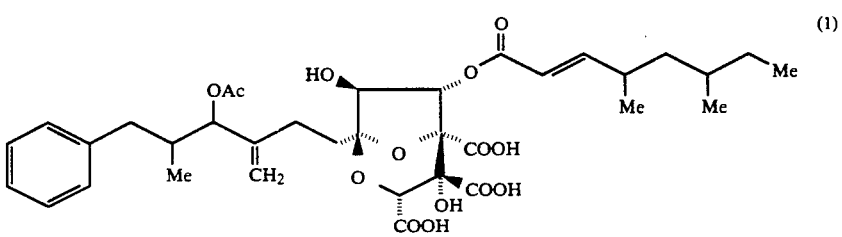

and

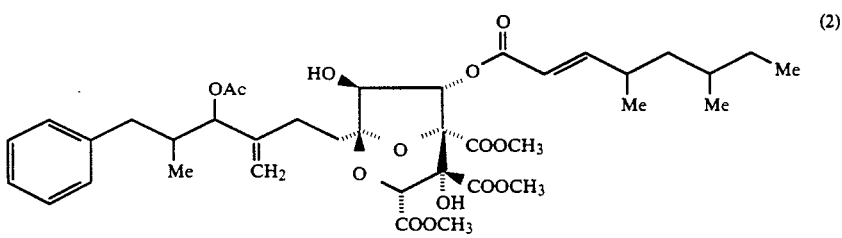

10. A pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

11. A method of treating hypercholesterolemia comprising the administration to a subject in need of such treatment a nontoxic therapeutically effective amount of a compound of claim 1.

12. A method of claim 11 wherein the therapeutically effective compound is selected from the group consisting of:

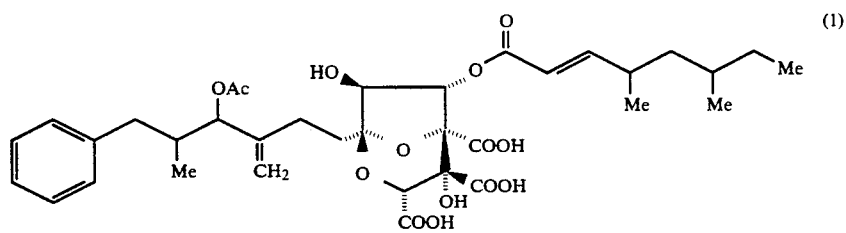

and

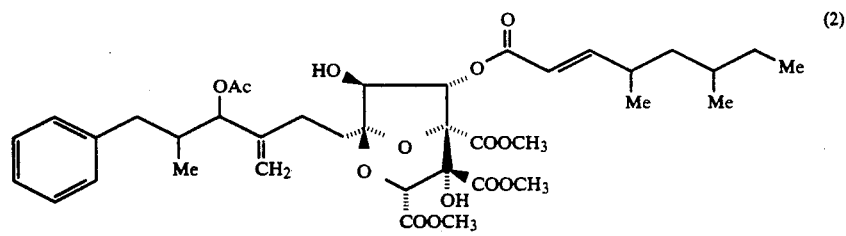

13. A method of inhibiting squalene synthetase comprising the administration to a subject in need of such treatment a nontoxic therapeutically effective amount of a compound of claim 1.

14. A method of claim 13 wherein the therapeutically effective compound is selected from the group consisting of:

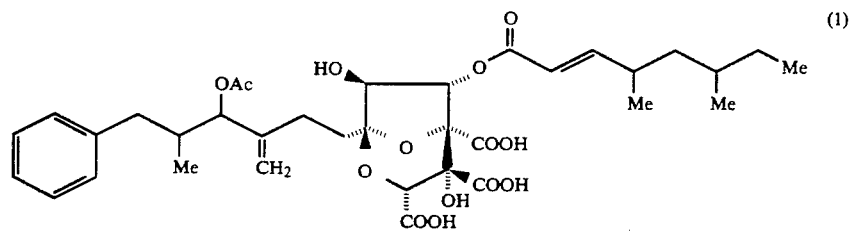
and
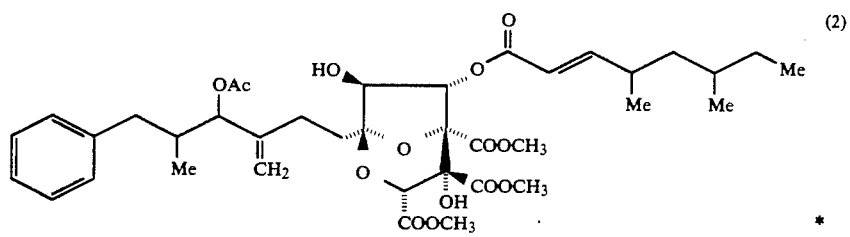
* * * * *